(12) United States Patent
Blakely et al.

(10) Patent No.: US 7,879,899 B2
(45) Date of Patent: Feb. 1, 2011

(54) INJECTABLE VETERINARY COMPOSITION FOR SMALL ANIMALS

(75) Inventors: William Blakely, Newry (IE); Lillian Cromie, Newry (IE); Sean Duffy, Newry (IE)

(73) Assignee: Norbrook Laboratories Limited, Newry, County Down (IE)

( * ) Notice: Subject to any disclaimer, the term of this patent is extended or adjusted under 35 U.S.C. 154(b) by 1105 days.

(21) Appl. No.: 10/510,204

(22) PCT Filed: Mar. 31, 2003

(86) PCT No.: PCT/GB03/01404

§ 371 (c)(1),
(2), (4) Date: Feb. 15, 2005

(87) PCT Pub. No.: WO03/082340

PCT Pub. Date: Oct. 9, 2003

(65) Prior Publication Data

US 2005/0147680 A1 Jul. 7, 2005

(30) Foreign Application Priority Data

Apr. 2, 2002 (GB) .................................. 0207529.9

(51) Int. Cl.
*A01N 43/38* (2006.01)
*A61K 31/40* (2006.01)

(52) U.S. Cl. ..................................................... 514/411

(58) Field of Classification Search .................. 514/411
See application file for complete search history.

(56) References Cited

U.S. PATENT DOCUMENTS 5,283,067 A 2/1994 Geller et al.

(Continued)

FOREIGN PATENT DOCUMENTS

CH 663 788 A5 1/1988

(Continued)

OTHER PUBLICATIONS

Jackson, T.W., et al., "Correlation of Serum Ibuprofen Concentration with Clinical Signs of Toxicity in Three Canine Exposures", *Vet Hum Toxicol*, vol. 33, No. 5, pp. 486-488, (1991).

(Continued)

*Primary Examiner*—Frederick Krass
*Assistant Examiner*—Benjamin Packard
(74) *Attorney, Agent, or Firm*—The Nath Law Group; Joshua B. Goldberg; Tanya E. Harkins

(57) ABSTRACT

An injectable aqueous composition for veterinary use containing a non-steroidal anti-inflammatory compound in an amount of from about 0.25 to 30% (w/v) together with a physiologically acceptable oxygenated polymeric surfactant in an amount of from about 0.5 to 20% (w/v).

18 Claims, 1 Drawing Sheet

Figure 1:
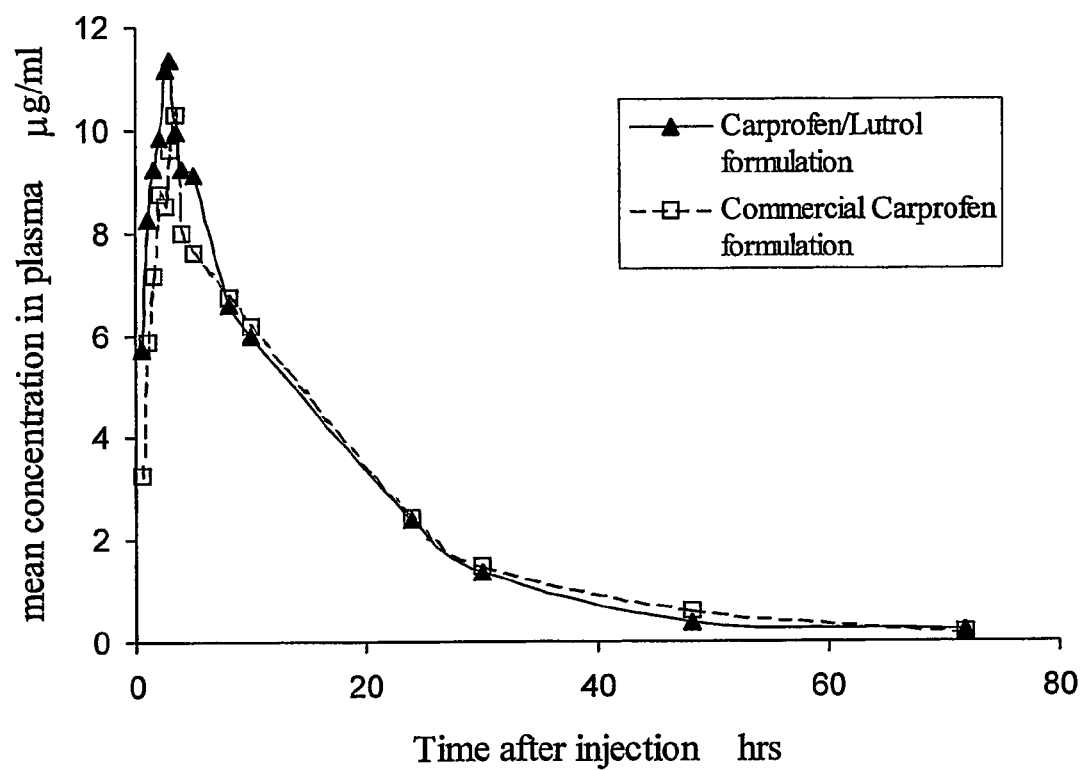

U.S. PATENT DOCUMENTS 5,434,170 A * 7/1995 Andrulis, Jr. ................ 514/323
5,527,832 A * 6/1996 Chi et al. ................ 514/772.4
2001/0049363 A1   12/2001 Rubin et al.

FOREIGN PATENT DOCUMENTS

| EP | 663788 | * | 1/1988 |
| EP | 0 756 870 A2 | | 2/1997 |
| EP | 0 955 063 A1 | | 11/1999 |
| EP | 0955063 | * | 11/1999 |
| WO | 02/074282 A1 | | 9/2002 |
| WO | 03/053430 A1 | | 7/2003 |

OTHER PUBLICATIONS

Tsuchiya, Y., et al., "Early Pathophysiological Features in Canine Renal Papillary Necrosis Induced by Nefiracetam", Toxicol Pathol, vol. 33, No. 5, pp. 561-569, (2005).

Poortinga, E.W., et al., "A case-control study of acute ibuprofen toxicity in dogs", Prev Vet Med, vol. 35, No. 2, pp. 115-124, (1998).

RIMADYL, Product Description: Indications; Dosage and Administration, 2 pages, Sep. 2005.

* cited by examiner

INJECTABLE VETERINARY COMPOSITION FOR SMALL ANIMALS

This invention relates to the use of non-steroidal anti-inflammatory drugs (NSAIDs), particularly the formulation of such drugs in solutions suitable for injection, especially for use in veterinary medicine for the purposes of treating small animals, such as companion animals.

BACKGROUND OF THE INVENTION

Non-steroidal anti-inflammatory drugs find wide application in the treatment of inflammatory conditions and the alleviation of pain in veterinary and human medicine. Such drugs are often characterised by the presence of a carboxylic acid function or derivative thereof. Examples of such non-steroidal anti-inflammatories include carprofen, ibuprofen, ketoprofen, benoxaprofen, naproxen, sulindac, zomepirac, fenclofenac alcofenac, ibufenac, flunixin and indomethacin. The administration of such compounds parenterally can present the difficulty of local irritation and induce haemolytic side effects.

In EP-A-0 280 887, Ferro and Steffen teach the formulation of NSAIDs, by utilising salts of cholanic acid and certain lipids to form mixed micelles in aqueous systems. These compositions have reduced side effects, in comparison with conventional formulations, when administered by injection to dogs.

OBJECTS OF THE INVENTION

It is an object of the present invention to provide novel pharmaceutical preparations of non-steroidal anti-inflammatory drugs suitable for injection. It is a further object of the invention to provide such preparations adapted for the provision of analgesia in small animals, especially companion animals.

SUMMARY OF THE INVENTION

It has been surprisingly found that NSAIDs, preferably carprofen (6-chloro-α-methyl-carbazole-2-acetic acid) or a salt thereof, most preferably carprofen in the form of its arginine or lysine salt, can be readily formulated in aqueous systems by the use of certain pharmaceutically acceptable synthetic polymer agents to the effect that the problems of local irritancy and haemolysis associated with conventional formulations of these drugs are avoided or at least greatly reduced.

Accordingly, the aforesaid objects are achievable by this invention which provides an injectable aqueous composition for veterinary use containing an effective amount of a non-steroidal anti-inflammatory compound together with a physiologically acceptable oxygenated polymeric surfactant.

An additional technical benefit in comparison with formulations utilising the prior art cholanic acid/lipid solubilising method is also achieved by the present invention which offers enhanced stability at room temperature.

Polyoxypropylene/polyoxyethylene block co-polymers (poloxamers) or derivatives thereof are the preferred polymeric agents used for the purposes of the invention as illustrated in the following examples for a composition containing carprofen or physiologically acceptable salts thereof as the active ingredient. Such a solution is especially useful in veterinary medicine for a variety of analgesic, anti-pyretic, and anti-inflammatory purposes such as the treatment of, musculo-skeletal and visceral pain in horses, pre- and post-operative pain in cats and dogs and of acute inflammation associated with respiratory disease.

The amount of NSAID that can be accommodated in the injection solutions of the present invention can vary over wide limits, for example from 0.5 to 30% (w/v), depending on the required dose for effective treatment of the subject. The quantity of poloxamer can also vary over wide limits, for example 0.5 to 20% (w/v), the upper limit for a given formulation being determined by viscosity considerations. In normal use the solution may be readily administered by conventional hypodermic syringe.

The present invention provides another means of formulating NSAID's in aqueous solution, in a form that is suitable for parenteral administration to animals or humans, especially companion animals such as cats and dogs. The compositions of the present invention provide simpler formulations than those of EP 0 280 887, without the requirement for lipids and cholanic acids. It is a further feature of these simpler formulations that they remain stable, without the anticipated precipitation or turbidity and can be stored at room temperature, contrasting with the cholanic acid/lipid formulation, which typically requires refrigerated storage (2-8 C).

The non-steroidal anti-inflammatory compound may be present in an amount of from about 2.5 to 7.5% (w/v) or more, preferably 2.5 to 5% (w/v). However, it will be understood by those skilled in the art that a useful lower range of from about 0.25% (w/v) may be employed where small volume changes in delivery volume are not significant, e.g. in treating felines with a non-steroidal anti-inflammatory compound such as carprofen.

Arginine may be present in an amount from about 1% to 20% (w/v).

The poloxamers are generally present in an amount of from about 2 to 12% (w/v). Moreover an organic solvent can be also present with the poloxamer, generally in the range of about 0.5 to 20% (w/v), in which case the poloxamers can be present in an amount from 1% to 12% (w/v).

A poloxamer generally confirms to the formula $HO(CH_2CH_2O)_x(CCH_3HCH_2O)_y(CH_2CH_2)_zH$, wherein x, y and z are variables which are independently and selectively controllable. The values of x, y and z are respectively whole numbers in the range 2 to 128 and represent target values which will vary slightly according to commercial sources. An example of a preferred poloxamer is $HO(CH_2CH_2O)_{75}(CCH_3HCH_2O)_{30}(CH_2CH_2)_{75}H$.

The present invention provides an aqueous injectable composition comprising carprofen or a physiologically acceptable salt thereof in an amount of from at least 0.25%, preferably 0.5% to 30% (w/v), a polymeric species selected from the group of polyoxypropylene/polyoxyethylene block co-polymers in the amount of from 0.5% to 20% (w/v), a preservative and water sufficient for injection.

According to the invention there is also provided a method of producing a room-temperature stable injectable aqueous composition for veterinary use comprising bringing together carprofen or a physiologically acceptable salt and a poloxamer, and adding sufficient water for injection. Additionally preservatives may also be included. Preferably the poloxamer is $HO(CH_2CH_2O)_{75}(CCH_3HCH_2O)_{30}(CH_2CH_2)_{75}H$.

Furthermore the invention also relates to the use of polyoxypropylene/polyoxyethylene block co-polymers for the manufacture of locally tolerable aqueous injection solutions of non-steroidal compounds.

MODE FOR PERFORMANCE OF THE INVENTION

The invention will now be described further by way of illustrative example with reference to the accompanying FIGURE, which represents data showing the mean levels of carprofen found in the blood plasma of dogs following administration of a formulation of the invention.

EXAMPLES

Example 1

A suitable formulation of carprofen, in this embodiment provided as its arginine salt, can be made by bringing together, following standard industry procedures, the following ingredients to form a mixture which is brought up to injection volume by addition of an appropriate amount of water for injection:

Carprofen 5.0% w/v
L-Arginine EP 3.1% w/v
Lutrol F68 (poloxamer 188, NF, EP) 5.0% w/v
Nipagin M (BP, EP, USP/NF) 0.15% w/v (preservative)
Water for injection ad 100% w/v Other examples of suitable formulations include:

Example 2

Carprofen 5.0% w/v
L-Arginine EP 3% w/v
Lutrol F68 (poloxamer 188, NF EP) 10% w/v
Propylene Glycol 20% w/v
Water for injection ad 100% w/v

Example 3

Carprofen 5.0% w/v
L-Arginine EP 3% w/v
Lutrol F68 (poloxamer 188, NF EP) 2.4% w/v
Propylene Glycol 20% w/v
Water for injection ad 100% w/v

Example 4

Carprofen 5.0% w/v
L-Arginine EP 3% w/v
Lutrol F68 (poloxamer 188, NF EP) 12% w/v
Propylene Glycol 20% w/v
Water for injection ad 100% w/v

Example 5

Carprofen 5.0% w/v
L-Arginine EP 3% w/v
Lutrol F68 (poloxamer 188, NF EP) 3.5% w/v
Propylene Glycol 20% w/v
Water for injection ad 100% w/v

Example 6

Carprofen 5.0% w/v
L-Arginine EP 3.1% w/v
Lutrol F68 (poloxamer 188, NF EP) 5% w/v
Propylene Glycol 20% w/v
Water for injection ad 100% w/v

Example 7

Carprofen 5.0% w/v
L-Arginine EP 3.1% w/v
Lutrol F68 (poloxamer 188, NF EP) 5% w/v
Water for injection ad 100% w/v

Example 8

Carprofen 5.0% w/v
L-Arginine EP 3.1% w/v
Lutrol F68 (poloxamer 188, NF EP) 7% w/v
Propylene Glycol 20% w/v
Water for injection ad 100% w/v

Example 9

Carprofen 5.0% w/v
L-Arginine EP 3.1% w/v
Lutrol F68 (poloxamer 188, NF EP) 5% w/v
Benzyl Alcohol 1% w/v
Water for injection ad 100% w/v

Example 10

Carprofen 5.0% w/v
L-Arginine EP 3.1% w/v
Lutrol F68 (poloxamer 188, NF EP) 6% w/v
Water for injection ad 100% w/v

Example 11

Carprofen 5.0% w/v
L-Arginine EP 3% w/v
Lutrol F68 (poloxamer 188, NF EP) 5% w/v
Benzyl Alcohol 1% w/v
Water for injection ad 100% w/v

Example 12

Carprofen 5.0% w/v
L-Arginine EP 3.1% w/v
Lutrol F68 (poloxamer 188, NF EP) 5% w/v
Benzyl Alcohol 0.3% w/v
Water for injection ad 100% w/v

Example 13

Carprofen 5.0% w/v
L-Arginine EP 2.7% w/v
Lutrol F68 (poloxamer 188, NF EP) 5% w/v
Benzyl Alcohol 1% w/v
Water for injection ad 100% w/v

Example 14

Carprofen 5.0% w/v
L-Arginine EP 3.3% w/v
Lutrol F68 (poloxamer 188, NF EP) 5% w/v Benzyl Alcohol 1% w/v
Water for injection ad 100% w/v Example 15

Carprofen 5.0% w/v
L-Arginine EP 3.1% w/v
Lutrol F68 (poloxamer 188, NF EP) 5% w/v
Benzyl Alcohol 1% w/v
SFS 0.25% w/v
Water for injection ad 100% w/v Example 16

Carprofen 5.0% w/v
L-Arginine EP 3.1% w/v
Lutrol F68 (poloxamer 188, NF EP) 5% w/v
Benzyl Alcohol 1% w/v
SFS 0.1% w/v
Water for injection ad 100% w/v Example 17

Carprofen 5.0% w/v
L-Arginine EP 3.1% w/v
Lutrol F68 (poloxamer 188, NF EP) 5% w/v
Benzyl Alcohol 1% w/v
SFS 0.4% w/v
Water for injection ad 100% w/v Example 18

Carprofen 5.0% w/v
L-Arginine EP 2.5% w/v
Lutrol F68 (poloxamer 188, NF EP) 5% w/v
Benzyl Alcohol 1% w/v
SFS 0.25% w/v
Water for injection ad 100% w/v Example 19

Carprofen 5.0% w/v
L-Arginine EP 3.1% w/v
Lutrol F68 (poloxamer 188, NF EP) 3% w/v
Benzyl Alcohol 1% w/v
SFS 0.25% w/v
Water for injection ad 100% w/v Examples of formulations which failed to achieve satisfactory commercial objectives are shown below:

Comparative Example 1

Carprofen 5.0% w/v
L-Arginine EP 3% w/v
Lutrol F68 (poloxamer 188, NF EP) 20% w/v
Propylene Glycol 20% w/v
Water for injection ad 100% w/v Comparative Example 2

Carprofen 5.0% w/v
L-Arginine EP 3.1% w/v
Lutrol F68 (poloxamer 188, NF EP) 2% w/v
Benzyl Alcohol 1% w/v
SFS 0.25% w/v
Water for injection ad 100% w/v A comparison was made with the prior art formulation (derived from EP 0 280 887) that uses about 26% (w/v), of cholanic acid and lecithin, in a similar strength carprofen formulation. This formulation demonstrates bioequivalence to the aforesaid cholanic acid/lipid formulations but utilises only 5% (w/v) of the inventive polymeric surfactant additive. Thus compositions of the present invention can substantially reduce the burden of auxiliary ingredients injected into the subject on treatment. These formulations have also been found to have low side effects, with no injection site reactions such as swelling, hardness, softness, heat, redness or pain being observed during studies involving dogs.

A further benefit of compositions according to the invention is that of room temperature stability. A trial lot of the formulation given in the example has been studied over a period of eleven months at ambient temperatures without loss of potency being observed. The trial lot was assayed as containing 5.16% carprofen on manufacture, 5.10% after seven months, and 5.26% after eleven months, these apparent differences being accounted for by slight moisture loss. Currently available formulations typically require controlled chilled storage at 2-8 C, i.e. refrigeration, cool room, or chiller cabinet storage.

A study was undertaken with a view to evaluating the mean levels of carprofen found in dogs following the administration of a dose of approximately 4 mg/kg of a composition according to the Example in comparison with results obtained by administration of a commercially available product of comparable strength.

The results of the pharmacokinetic study are tabulated below and shown graphically in FIG. 1. The Table compares the mean plasma concentrations of carprofen found in dogs after subcutaneous injection of carprofen at a dose of approximately 4 mg/kg using a commercially available formulation, and using the formulation given in the Example. Statistical analysis of these results confirmed bioequivalence in accordance with European Guidelines (Volume 8 of EMEA/CVMP/016-00/Final).

TABLE 1

| Time after injection (hours) | Carprofen/Lutrol formulation (μg/ml) | Commercially available Carprofen formulation (μg/ml) |
| --- | --- | --- |
| 0.5 | 5.73 | 3.27 |
| 1 | 8.24 | 5.86 |
| 1.5 | 9.24 | 7.16 |
| 2 | 9.85 | 8.76 |
| 2.5 | 11.18 | 8.53 |
| 3 | 11.36 | 9.63 |
| 3.5 | 9.94 | 10.29 |
| 4 | 9.23 | 7.99 |
| 5 | 9.12 | 7.6 |
| 8 | 6.57 | 6.75 |
| 10 | 5.98 | 6.18 |
| 24 | 2.39 | 2.41 |
| 30 | 1.37 | 1.48 |
| 48 | 0.39 | 0.6 |
| 72 | 0.23 | 0.18 |

The invention claimed is:

1. A room-temperature stable injectable solution comprising from 0.25 to 30% (w/v) of 6-chloro-x-methyl-carbazole-2-acetic acid or a physiologically acceptable salt of 6-chloro-x-methyl-carbazole-2-acetic acid and from 0.5 to 20% (w/v) of a poloxamer, and water q.s. for injection.

2. An injectable aqueous solution according to claim 1, wherein the 6-chloro-x-methyl-carbazole-2-acetic acid salt is in the form of an arginine salt.

3. An injectable aqueous solution according to claim 1, wherein the 6-chloro-x-methyl-carbazole-2-acetic acid salt is in the form of a lysine salt.

4. An injectable aqueous solution according to claim 1, wherein 6-chloro-x-methyl-carbazole-2-acetic acid is present in an amount of from 2.5 to 7.5% (w/v).

5. An injectable aqueous solution according to claim 1, wherein 6-chloro-x-methyl-carbazole-2-acetic acid is present in an amount of from 2.5 to 5% (w/v).

6. An injectable aqueous solution according to claim 1, comprising arginine in an amount of from 1 to 20% (w/v).

7. An injectable aqueous solution according to claim 1, wherein an organic solvent is present with the poloxamer.

8. An injectable aqueous solution according to claim 7, wherein the organic solvent is present in the range of 0.5 to 20% (w/v).

9. An injectable aqueous solution according to claim 1, wherein the poloxamer is $HO(CH_2CH_2O)_x(CCH_3HCH_2O)_y(CH_2CH_2)_zH$ wherein x is 75, y is 30 and z is 75.

10. A method of producing a room-temperature stable injectable aqueous solution, comprising:
dissolving 6-chloro-x-methyl-carbazole-2-acetic acid or a physiologically acceptable salt thereof and a poloxamer in water to obtain an injectable solution comprising from 0.25 to 30% (w/v) of 6-chloro-x-methyl-carbazole-2-acetic acid or a physiologically acceptable salt of 6-chloro-x-methyl-carbazole-2-acetic acid, and from 0.5% to 20% (w/v) of poloxamer.

11. A method according to claim 10, wherein the poloxamer is $HO(CH_2CH_2O)_x(CCH_3HCH_2O)_y(CH_2CH_2)_zH$ wherein x is 75, y is 30 and z is 75.

12. A method of producing an injectable aqueous solution according to claim 10, wherein said method further comprises the inclusion of a preservative.

13. An injectable aqueous solution for veterinary use comprising 6-chloro-x-methyl-carbazole-2-acetic acid 5.0% w/v, arginine 3.1% w/v, poloxamer 5.0% w/v, preservative 0.15% w/v and water q.s.

14. A method of producing an injectable aqueous solution comprising bringing together 6-chloro-x-methyl-carbazole-2-acetic acid 5.0% w/v, arginine 3.1% w/v, poloxamer 5.0% w/v, preservative 0.15% w/v and water q.s to form a mixture.

15. A method of producing an injectable aqueous solution according to claim 11, wherein said method further comprises the inclusion of a preservative.

16. An injectable aqueous solution according to claim 1, comprising from about 0.5 to about 30% (w/v) of 6-chloro-x-methyl-carbazole-2-acetic acid or a physiologically acceptable salt of 6-chloro-x-methyl-carbazole-2-acetic acid.

17. A method of treating inflammation in felines comprising administering the injectable aqueous anti-inflammatory solution of claim 1.

18. The injectable aqueous solution according to claim 1, wherein the injectable aqueous solution is free from precipitate.

* * * * *